United States Patent
Nelson et al.

(10) Patent No.: US 8,249,827 B2
(45) Date of Patent: Aug. 21, 2012

(54) METHOD AND SYSTEM FOR HEATER SIGNATURE DETECTION DIAGNOSTICS OF A PARTICULATE MATTER SENSOR

(75) Inventors: Charles Scott Nelson, Fenton, MI (US); Lary R. Hocken, Davison, MI (US)

(73) Assignee: Delphi Technologies, Inc., Troy, MI (US)

( * ) Notice: Subject to any disclaimer, the term of this patent is extended or adjusted under 35 U.S.C. 154(b) by 402 days.

(21) Appl. No.: 12/614,654

(22) Filed: Nov. 9, 2009

(65) Prior Publication Data

US 2011/0109331 A1    May 12, 2011

(51) Int. Cl.
*G01N 27/14* (2006.01)
*G06F 11/30* (2006.01)
*G06F 19/00* (2012.01)

(52) U.S. Cl. ......... 702/183; 73/865.8; 324/71.1; 702/1; 702/127; 702/182; 708/200

(58) Field of Classification Search ............... 73/732.1, 73/865.8, 866; 324/71.1, 451, 452, 459, 324/464; 374/45; 702/1, 33, 127, 182, 183, 702/187, 189; 708/100, 105, 200
See application file for complete search history.

(56) References Cited

U.S. PATENT DOCUMENTS

| | | | |
|---|---|---|---|
| 4,656,832 A | 4/1987 | Yukihisa et al. | |
| 6,634,210 B1 | 10/2003 | Bosch et al. | |
| 7,325,457 B2* | 2/2008 | Fujimori et al. | 73/724 |
| 2002/0060150 A1 | 5/2002 | Hashimoto et al. | |
| 2003/0184309 A1* | 10/2003 | Lurtz | 324/525 |
| 2003/0196499 A1* | 10/2003 | Bosch et al. | 73/865.5 |
| 2007/0068266 A1* | 3/2007 | Fujimori et al. | 73/724 |
| 2008/0282769 A1 | 11/2008 | Nelson | |
| 2008/0283398 A1 | 11/2008 | Nelson et al. | |
| 2009/0090622 A1 | 4/2009 | Ripley | |
| 2009/0126458 A1 | 5/2009 | Fleischer et al. | |
| 2009/0139081 A1 | 6/2009 | Nelson | |

(Continued)

FOREIGN PATENT DOCUMENTS

DE    28 35 008    2/1980

(Continued)

OTHER PUBLICATIONS

European Search Report for EP 10 18 7922 dated Feb. 18, 2011.

(Continued)

*Primary Examiner* — Edward Cosimano
(74) *Attorney, Agent, or Firm* — Mark H. Svoboda

(57) ABSTRACT

A diagnostic method and system is described for diagnosing an operating condition of a conductive particulate matter sensor. The sensor has a substrate with electrical resistance that varies with temperature and two electrodes on the substrate adapted to collect particulate matter between the electrodes, thereby establishing an electrically conductive path through collected particulate matter between the electrodes that can be detected by measuring electrical resistance between the electrodes, $R_{elect}$. The diagnosis is performed by heating the substrate in the area between the electrodes and detecting whether resistance varies with temperature as expected, and then cooling the substrate back down and detecting whether resistance varies with temperature as expected. If resistance varies as expected during both heating and cooling, then a validation is diagnosed that the sensor is in proper operating condition if resistance increases in a manner consistent with evaporation of condensate. If resistance does not vary as expected, then a failure condition is diagnosed.

8 Claims, 4 Drawing Sheets

U.S. PATENT DOCUMENTS

| | | |
|---|---|---|
| 2010/0280768 A1* | 11/2010 | Bohan et al. .................. 702/50 |
| 2010/0280788 A1* | 11/2010 | Bohan et al. ................. 702/130 |
| 2010/0312488 A1 | 12/2010 | Diehl et al. |
| 2011/0107815 A1* | 5/2011 | Nelson et al. ................ 73/23.33 |

FOREIGN PATENT DOCUMENTS

| | | |
|---|---|---|
| DE | 10 2005 030 134 | 1/2007 |
| DE | 10 2007 047 081 | 4/2009 |
| EP | 2 065 903 | 9/2009 |
| EP | 2320220 A1 * | 5/2011 |

OTHER PUBLICATIONS

European Search Report for EP 10 18 7923 dated Feb. 18, 2011.

* cited by examiner

US 8,249,827 B2

METHOD AND SYSTEM FOR HEATER SIGNATURE DETECTION DIAGNOSTICS OF A PARTICULATE MATTER SENSOR

BACKGROUND OF THE INVENTION

This invention relates generally to sensors for detecting electrically conductive particulate matter, such as soot, and more particularly to a method and system for diagnosing potential failure modes in such sensors.

Incomplete combustion of certain heavy hydrocarbon compounds, such as heavy oils, diesel fuel, and the like may lead to particulate formation (e.g., soot). In the operation of internal combustion engines, excessive particulate formation can lead to "smoking" of the engine, which causes air pollution even though the carbon monoxide, hydrocarbons, and other pollutant components of the gaseous state exhaust emissions may be relatively low. Emission regulations require many engines to limit the levels of particulate emissions, and various control technologies such as diesel particulate filters (DPF) have been employed for this purpose.

In order to monitor the emission of particulate matter in the exhaust streams of certain types of internal combustion engines, e.g., to assess the effectiveness of DPF's, it is known to provide a particulate sensor system for detecting the level of particulate concentration emitted from an exhaust gas. Various particulate sensors have been proposed, including those shown in U.S. Pat. No. 4,656,832 issued to Yukihisa et al., U.S. Pat. No. 6,634,210 issued to Bosch et al., U.S. Pat. Publ. No. 2008/0283398 A1, U.S. Pat. Publ. No. 2008/0282769 A1, and U.S. Pat. Publ. No. 2009/0139081 A1, the disclosures of each of which are hereby incorporated by reference in their entirety.

Particulate sensors such as those described above generally have a pair of spaced apart sensing electrodes disposed on a substrate. The sensing electrodes are coupled to a measurement circuit by way of electrically conductive leads. The operating principle of the particulate sensor is based on the conductivity of the particulates (e.g., soot) deposited on (or over) the sensing electrodes. The electrical resistance between the sensing electrodes is relatively high when the sensor is clean but such resistance decreases as soot particulates accumulate. These sensors also have a heater that can be selectively activated to burn off the soot particulates to "reset" the sensor to a known, base "clean" state.

However, for diagnostic purposes, it can be difficult to distinguish between various states that may occur during various engine operating conditions, such as between: (i) a faulty state such as when there is an electrical open circuit in the wiring leads, which presents as a very high resistance between the sensing electrodes, and (ii) a normal state, such as when a sensor has just been cleaned, which also presents as a very high resistance, or between (i) a false positive state such as where the sensor presents a low resistance due to some cause other than soot particulates, e.g., water vapor condensate on the electrodes, and (ii) an actual positive state such as where soot particulates on the electrodes lead to a low resistance measurement.

Accordingly, there is a need for particulate sensor diagnostics that can accurately distinguish between sensor states during various engine operating conditions.

SUMMARY OF THE INVENTION

The present invention relates to a method of diagnosing an operating condition of an electrically conductive particulate matter sensor where the sensor comprises a substrate having an electrical resistance that varies with temperature and two electrodes on the substrate adapted to collect particulate matter between the electrodes, thereby establishing an electrically conductive path through collected particulate matter between the electrodes that can be detected by measuring electrical resistance between the electrodes, $R_{elect}$. The method according to the invention comprises the steps of:

(a) providing heat to the sensor in an amount sufficient to modify the electrical resistance of the substrate, and detecting whether $R_{elect}$ changes in a manner consistent with heating of the substrate;

(b) if $R_{elect}$ increases in a manner consistent with heating of the substrate in step (a), then removing the heat provided in step (a) to cool the substrate;

(c) if $R_{elect}$ does not change in a manner consistent with heating of the substrate in step (a) or $R_{elect}$ does not change in a manner consistent with cooling of the substrate in step (b), then diagnosing a failure condition for the sensor; and (d) if $R_{elect}$ changes in a manner consistent with cooling of the substrate in step (b), then diagnosing a validation that the sensor is in proper working condition.

Exemplary embodiments of the invention also relate to a storage medium encoded with machine readable computer program code for diagnosing a failure condition of an electrically conductive particulate matter sensor as described above where the storage medium includes instructions for causing a computer to implement the above-described method.

Another exemplary embodiment of the invention relates to a diagnostic system for an electrically conductive particulate matter sensor as described above, the system comprising a microprocessor in communication with the sensor and a storage medium including instructions for causing the microprocessor to implement the above-described a method.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Referring now to the Figures, where the invention will be described with reference to specific embodiments, without limiting same.

In describing and claiming algorithms according to the invention, letters and naming conventions are arbitrarily employed to represent numerical values (e.g., $R_{OBD\_hot}$, $K_{R\_OBD\_on\_pct}$). These naming conventions are used solely to enhance the readability of the description of the invention, and are not intended to have any functional significance whatsoever. The representation of these numerical values is intended to be precisely the same as if, for example completely arbitrary descriptions (e.g., $R_1$, $R_2$, $K_1$, $K_2$) had been used. Additionally, it should be noted that in the practice of the invention, measurements of resistance between the electrodes may be made by applying a known current across the electrodes, measuring the voltage differential between the electrodes, and calculating the resistance using Ohm's law, as is well-known in the art. It would of course be possible to simply use the voltage values in place of resistance values in the algorithm of the invention by converting the various resistance constants and equations to voltage, and such alternative embodiments are considered to be within the scope of the invention.

Figure 1:
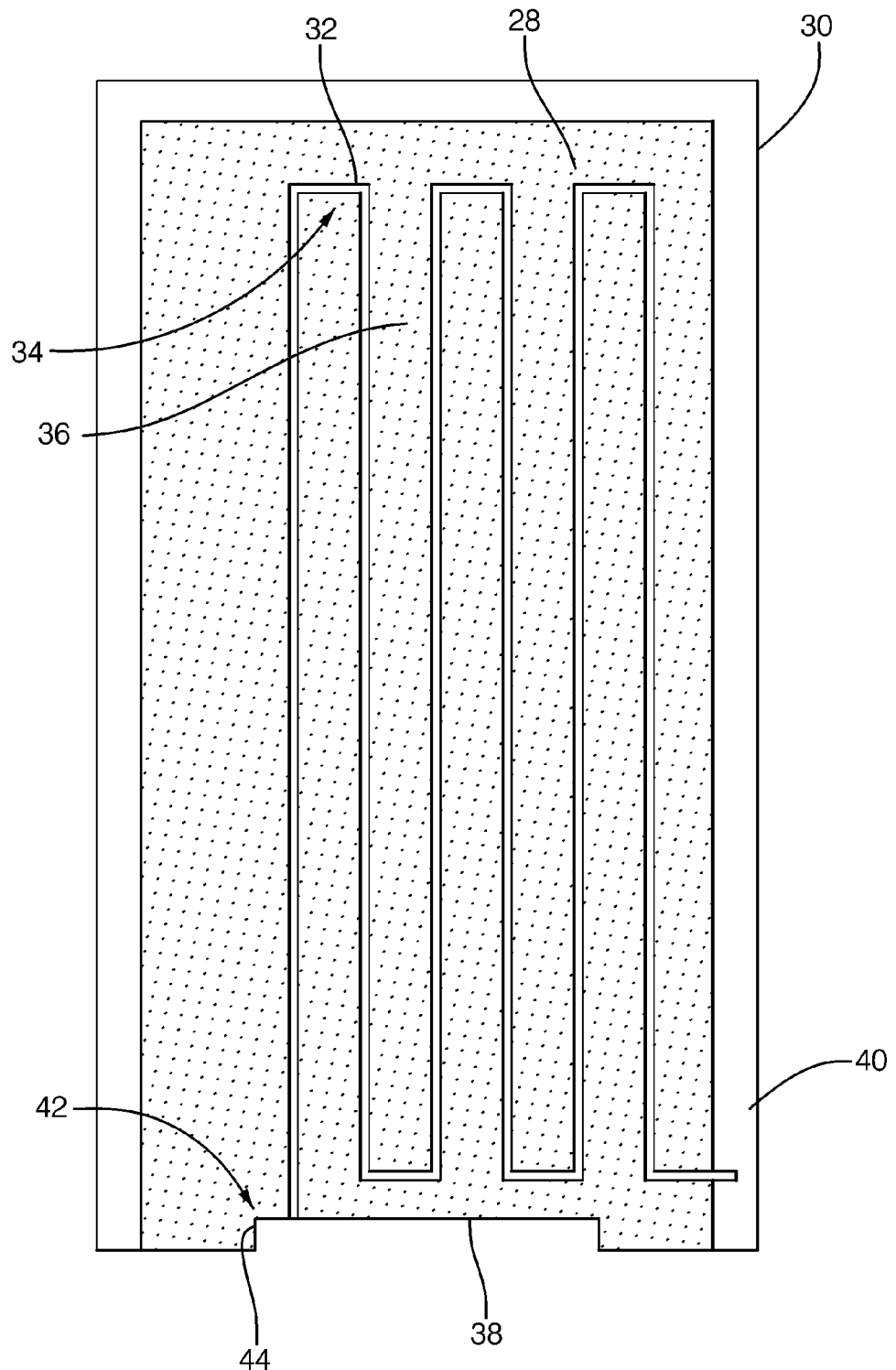
FIG. 1 is a top end view of a sensing element end useful in a sensor for which the diagnostics of the invention may be practiced.

FIG. 1 shows a top view of an exemplary particulate matter sensor that can be used in the practice of the present invention. In general, the sensor comprises a sensing element and a heating element, wherein the sensing element may comprise, but is not limited to, at least two sensing electrodes in proximity to each other on a substrate and configured so as to accumulate particulate matter therebetween, and wherein the heating element may comprise, but is not limited to, a temperature sensor, and a heater. The sensor may include a multi-layered structure comprising the sensing element, the temperature sensor, the heater, and a combination comprising at least one of the foregoing, contained in a single structure formed, e.g., by multi-layer technology.

The sensing electrodes can include metals, such as, gold, platinum, osmium, rhodium, iridium, ruthenium, aluminum, titanium, zirconium, and the like, as well as, oxides, cermets, alloys, and combinations comprising at least one of the foregoing metals. In an exemplary embodiment, the sensing electrode can comprise a platinum/alumina cermet wherein the platinum is about 90 wt % (weight percent) to about 98 wt % of the sensing electrode. In another exemplary embodiment, the sensing electrode comprises about 93 wt % to about 95 wt % platinum, where weight percent is based on the total dry weight of the cermet. Each sensing electrode may be composed of the same or different material as the other sensing electrode(s).

The sensing electrodes can be formulated in any fashion. In one exemplary embodiment, however, the sensing electrodes are formed by first preparing an ink paste by mixing an electrode forming-metal powder (e.g., platinum, gold, osmium, rhodium, iridium, ruthenium, aluminum, titanium, zirconium, and the like, or combinations of at least one of the foregoing) with oxides in a sufficient amount of solvent to attain a viscosity suitable for printing. The oxides used to form the sensing electrodes may include those oxides that do not promote the oxidation of particulates and that do not lower the burn-off temperature of the particulates. Non-suitable oxides are, e.g., copper oxide, cerium oxide, and iron oxide. The ink paste forming the sensing electrode can then be applied to an electrode substrate via sputtering, chemical vapor deposition, screen printing, flame spraying, lamination, stenciling, or the like.

The sensing electrodes may be disposed onto the electrode substrate such that a constant distance of separation between each sensing electrode is created. The width of the distance separating the sensing electrodes can vary widely, depending upon desired design parameters. In one exemplary embodiment, this distance comprises a width of separation of about 0.01 to about 0.12 millimeter (mm).

Both the heater and the temperature sensor, forming in whole or in part, the heating element, can comprise various materials. Possible materials include platinum, gold, palladium, and the like; and alloys, oxides, and combinations comprising at least one of the foregoing materials, with platinum/alumina, platinum/palladium, platinum, and palladium. The heater and temperature sensor can be applied to the sensor in any fashion, such as by sputtering, chemical vapor deposition, screen printing, flame spraying, lamination, and stenciling among others. In one embodiment, the heater can comprise a thickness of about 3 to about 50 micrometers. In another embodiment the heater thickness is about 5 to about 30 micrometers. In yet another embodiment, the heater thickness is about 10 to about 20 micrometers.

The sensor may further comprise various substrates useful in electrically isolating and protecting the sensing element and the heating element from the temperature surrounding the sensor and/or from the thermal reduction of the condensed particulates during the self-regeneration cycles. The substrates include, but are not limited to, an electrode protective layer, an electrode substrate, an isolation layer, an insulating temperature substrate, a heater substrate, insulating substrates, wherein the number of insulating substrates is sufficient to prevent disruptive ionic or electrical communication between the heating element and the sensing electrode (e.g., about 2 to about 3 insulating substrates), and combinations comprising at least one of the foregoing.

The substrates can comprise non-ionically conducting, electrically insulating materials. Possible electrically insulating materials include oxides, such as alumina, zirconia, yttria, lanthanum oxide, silica, and combinations comprising at least one of the foregoing, or any like material capable of inhibiting electrical communication and providing physical protection. In order to hinder electrical communication between the components of the sensor, the substrates may be composed of a high purity oxide; e.g., less than about 10.0 wt % impurities. In another embodiment, the substrates comprise less than about 8.0 wt % impurities. In yet another embodiment, the substrates comprise less than about 5.0 wt impurities, wherein the weight percent of the impurities is based on the total weight of the substrate. Although the composition of the individual substrates can vary, in certain embodiments they comprise a material having substantially similar coefficients of thermal expansion, shrinkage characteristics, and chemical compatibility in order to minimize, if not eliminate, delamination and other processing problems. Alkaline (e.g., sodium, potassium, lithium, and the like) oxides should be avoided as they can be easily reduced to form impurities in the heater, temperature sensor, and the sensing electrodes.

In general, each of the substrates can be of sufficient size to support the entire length of the sensing electrodes, the temperature sensor, and/or the heater. The thickness of each substrate can be determined based on the desired thermal response time of the self-regeneration cycle, where shorter thermal response times require a smaller thickness. The thickness of each substrate can be up to about 200 micrometers thick. In an exemplary embodiment, the substrate thickness is about 50 to about 180 micrometers. In another exemplary embodiment, the substrate thickness is about 140 to about 160 micrometers. The substrates can be formed using ceramic tape casting methods, and the like.

Any number of the substrates can be porous, dense, or both porous and dense. The porosity or the diameter of the pores can be controlled to limit the various sizes of particulates that can reach the sensing electrodes, and to limit the size of particulates that can penetrate and trap within the porous layer. In general, larger-sized particulates (e.g., particles having a diameter along the major axis equal to or greater than about 5 micrometers) interfere with current conduction more than do smaller-sized particulates (e.g., particles having a diameter along the major axis less than about 5 micrometers). Therefore, where more precise conductance measurements are desired, it is especially desirable to exclude the larger particulates from accumulating onto or between the sensing electrodes. Such exclusion can be achieved by controlling the size and/or the number of pores on the substrate, and/or by controlling the internal tortuousness of the substrate. Here, tortuousness is defined as the effective path length through the connected pores per standard thickness of the layer.

Pore size can be controlled by the size of the fugitive materials used, e.g., by controlling the size of carbon black or graphite, where fugitive materials are those materials that burn off at high temperatures leaving behind pores with controlled sizes. Tortuousness depends on the texture of the substrate-forming oxide powder used to form the substrate. Texture, in turn, can be controlled by firing the substrate-forming oxide powder at a high temperature to coarsen the substrate-forming powder, and then sieving the substrate-forming metal powder to the right size range for slurry making.

The sensor may further comprise various leads responsible for electrically communicating the sensor with the sensor circuit. One end of each sensing electrode, one end of the temperature sensor, and one end of the heater may have a connecting point to which one end of at least one lead may be attached. Each sensing electrode may be electrically connected with at least one lead extending from one end of each sensing electrode; and the heater is electrically connected with at least one lead extending from one end of the heater.

After acquiring the components of the sensor, the sensor may be constructed according to thick film multilayer technology such that the thickness of the sensor allows for good thermal response time toward the thermal cycle of sensor regeneration. In an exemplary embodiment, the sensor element thickness is about 0.1 to about 3.0 millimeter (mm).

Figure 2:
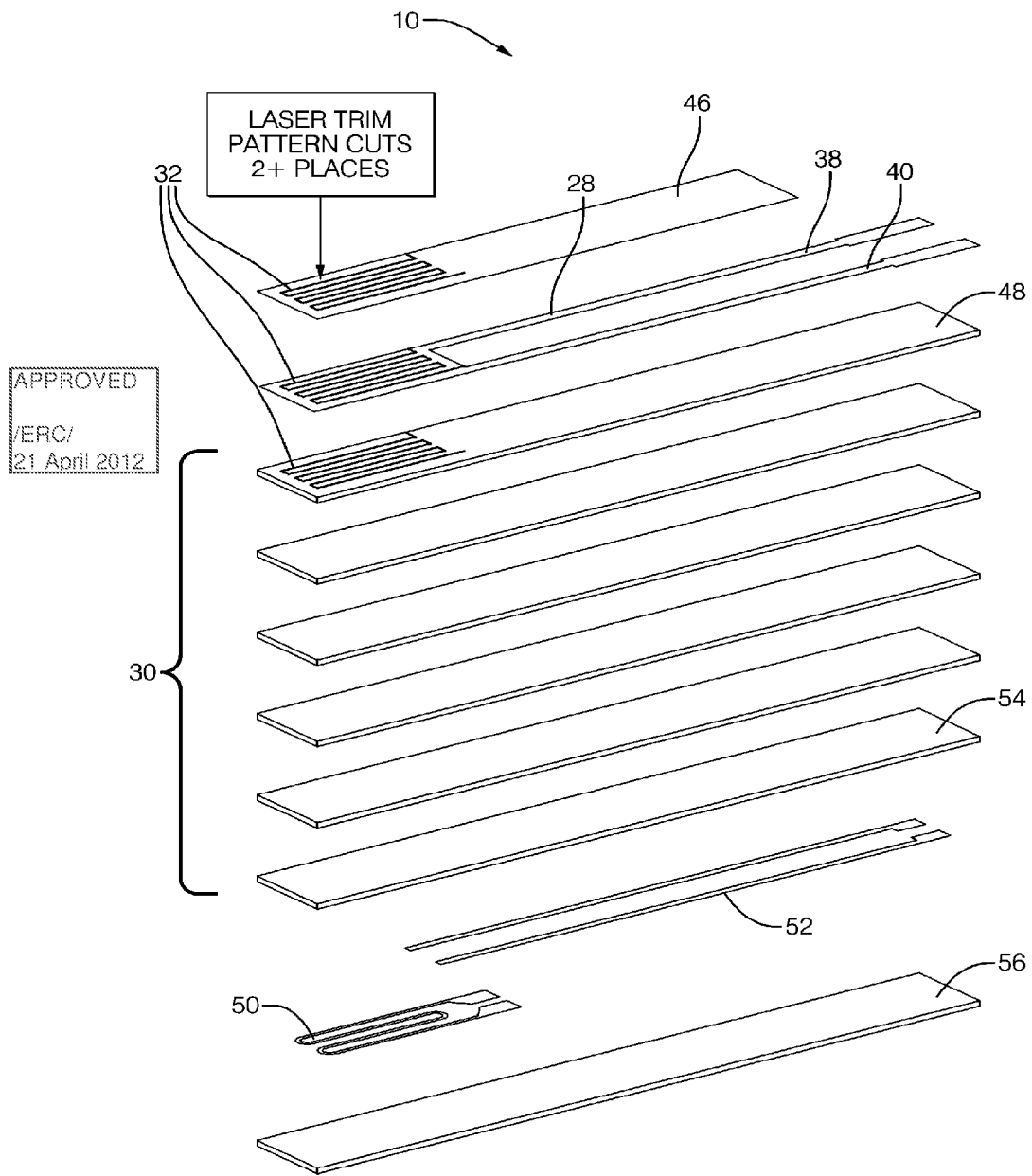
FIG. 2 is a schematic showing an exemplary sensor for which the diagnostics of the invention may be practiced.
Figure 4:
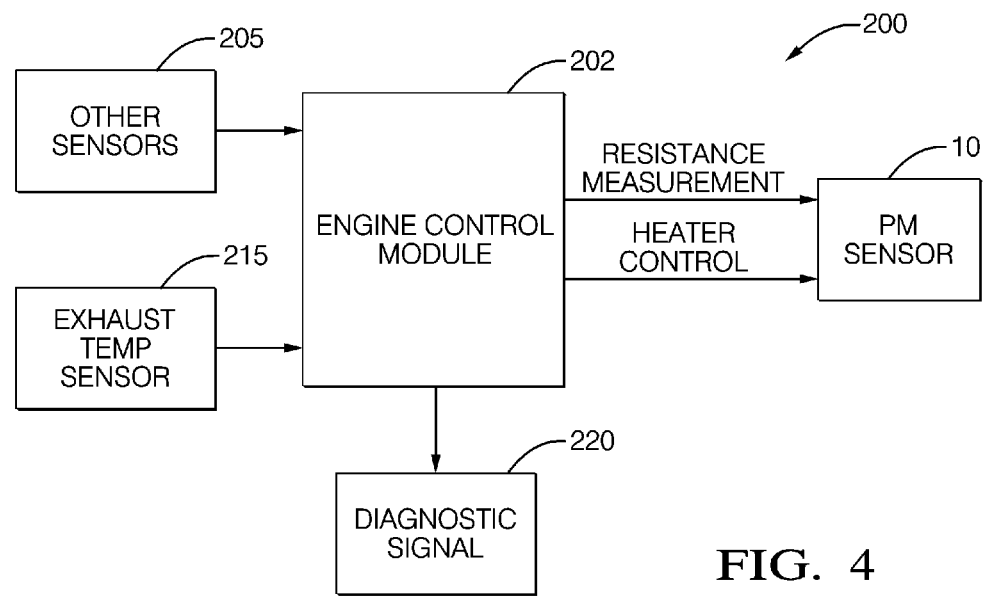
FIG. 4 is a schematic illustration of an engine control module and a particulate matter sensor.

Referring now to FIG. 1, FIG. 1 shows a sensing element pad 28 on a substrate 30 after a pattern 32 has been cut into the sensing element pad 28 with an ablating device. It will readily be appreciated that prior to ablating the portion of the sensing element pad 28 into which the pattern 32 is to be formed is a continuous solid parallelepiped-shaped layer. The pattern 32 establishes two separate winding or zig zag or inter-digitized fingers paths 34, 36 that are established without electrical connection between them, owing to the pattern 32. Each finger path 34, 36 is connected to a respective conductive lead 38, 40 as shown, with the leads 38, 40 being established by elongated legs of the sensing element pad 28 that extend away from the continuous area that bears the pattern 32. As shown at 42, the pattern 32 may begin at a location that is distanced from an edge 44 of the pad end of a conductive lead 38 to avoid tolerance stack-up Turning now to FIG. 2, FIG. 2 shows an exploded view of a complete soot sensor 10. As shown, the sensing element pad 28 may be deposited onto a multi-layer substrate 30 made of, e.g., HTCC tape. A protective layer 46 may be on the sensing element pad 28 as shown, and the ablating device may cut the pattern 32 in the protective layer 46, sensing element pad 28, and even into the top layer 48 of the multi-layer substrate 30 as shown. A heater 50 with heater leads 52 may be deposited or formed on a bottom layer 54 of the substrate 30 and covered with its own heater protective layer 56. The layers shown in FIG. 4 are substantially flush with each other and coterminous with each other, except that the pad protective layer 46 might not extend all the way to the end of the electrode legs 38, 40 of the sensing element pad 28 as shown.

Figure 3:
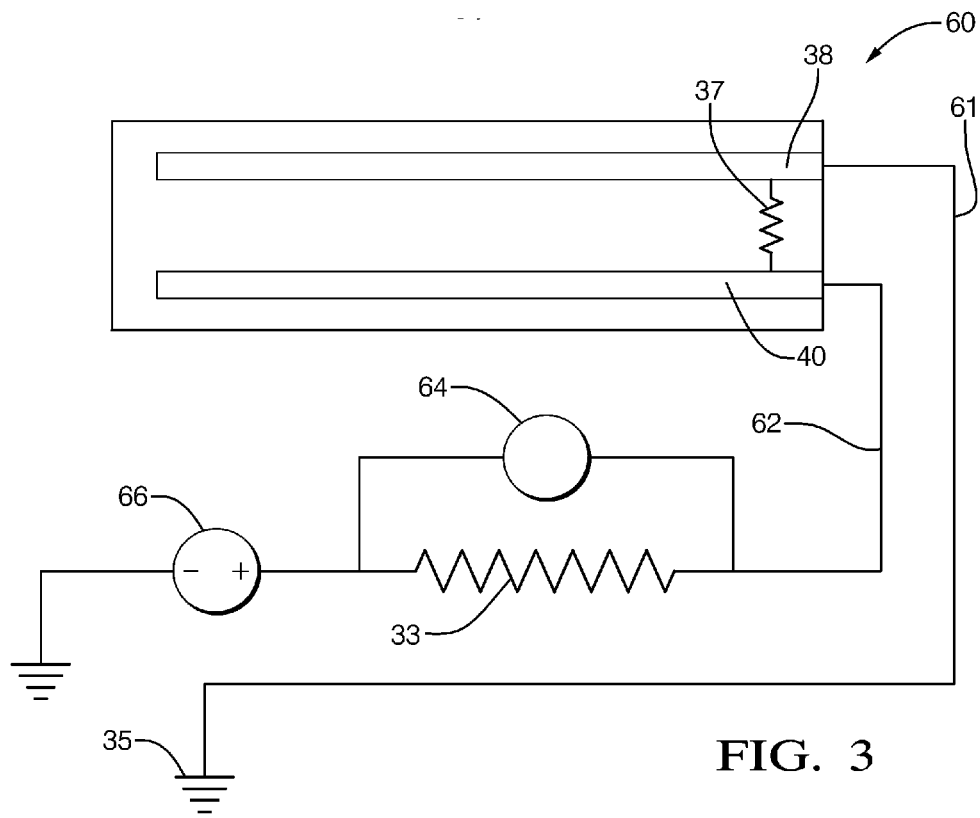
FIG. 3 is a circuit diagram showing a circuit for measuring resistance between electrodes of a particulate matter sensor.

FIG. 3 depicts an exemplary embodiment of an impedance measurement circuit 60. As shown in FIG. 3, the first measuring lead 38 is electrically communicated to a first lead 61. The first lead 61 extends from the electrical communication with the first measuring lead 38 to a ground potential 35. Additionally, a second lead 40 is electrically communicated to the second measuring lead 62. Optionally, a bias resistor 37 may be connected between leads 38 and 40 on the sensor in parallel with the sensing element electrodes in order to provide continuous monitoring for any continuity loss in the vehicle/sensor harness. In an exemplary embodiment, resistor 37 may be formed of known materials such as ruthenium oxide with a glass coating with post-element firing and laser trimmed. The second lead 62 extends from the electrical communication with the second measuring lead 40 to a resistor 33. The resistor 33, in turn, is electrically communicated to a DC voltage source 66, and to a measuring device 64. In an alternative exemplary embodiment, the resistor 33 and measuring device 64 can be configured with lead 61 to be in electrical communication with ground potential 35. The measuring device 64 can be any device capable of reading the resistance, such as a voltmeter, or an ohmmeter.

The method and system of the invention may be used in conjunction with a sensor for conductive particulate matter of any sort and in a variety of environments. In one exemplary embodiment, the sensor is a soot sensor in the exhaust stream of an internal combustion engine such as a diesel engine. Referring now to FIG. 4, a non-limiting example of a particulate sensor diagnostic system 200 is illustrated. The diagnostic system comprises a controller or an engine control module (ECM) 202. Alternatively to an ECM, a stand-alone diagnostic or combined sensor and diagnostic control module may be used, provided that it is able to communicate with an ECM in order to obtain information from the ECM, such as exhaust temperature, engine operating state, etc. ECM 202 comprises among other elements a microprocessor for receiving signals indicative of the vehicle performance as well as providing signals for control of various system components, read only memory in the form of an electronic storage medium for executable programs or algorithms and calibration values or constants, random access memory and data buses for allowing the necessary communications (e.g., input, output and within the ECM) with the ECM in accordance with known technologies.

In accordance with an exemplary embodiment the controller will comprise a microcontroller, microprocessor, or other equivalent processing device capable of executing commands of computer readable data or program for executing a control algorithm. In order to perform the prescribed functions and desired processing, as well as the computations therefore (e.g., the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

The ECM receives various signals from various sensors in order to determine the state of the engine as well as vary the operational state and perform diagnostics for example, the ECM can determine, based on its input from other sensors 205 and logic and control algorithms whether the engine is being started in a "cold start" state as well as perform and/or control other vehicle operations. Some of the sensors that may be included in other sensors 205 which provide input to the ECM 202 include but are not limited to the following: engine coolant temperature sensor, engine speed sensor, exhaust oxygen sensor, engine temperature, and the like. The sensors used may also be related in part to the type of engine being used (e.g., water cooled, air cooled, diesel, gas, hybrid, etc.). The ECM 202 also receives input from exhaust temperature sensor 215, which may be a temperature probe located in the exhaust stream in proximity to the particulate matter sensor 10 or other equivalent means or method for measuring the exhaust temperature.

In accordance with operating programs, algorithms, look up tables and constants resident upon the microcomputer of the ECM various output signals, including control of heater element 50 (part of particulate matter sensor 10) and diagnostic signal 220 are provided by the ECM. While the control signals for heater element 50 and diagnostic signal 220 are relevant to the practice of the invention, the ECM may also provide other control signals to control the engine (e.g., limiting or shutting off fuel flow as well as closing or opening the intake and exhaust valves of the engine) as well as performing other vehicle operations including but not limited to: fuel/air flow control to maintain optimum, lean or rich stoichiometry as may be required to provide the required torque output; spark timing; engine output; and providing on board malfunctioning diagnostic (OBD) means to the vehicle operator.

Figure 5:
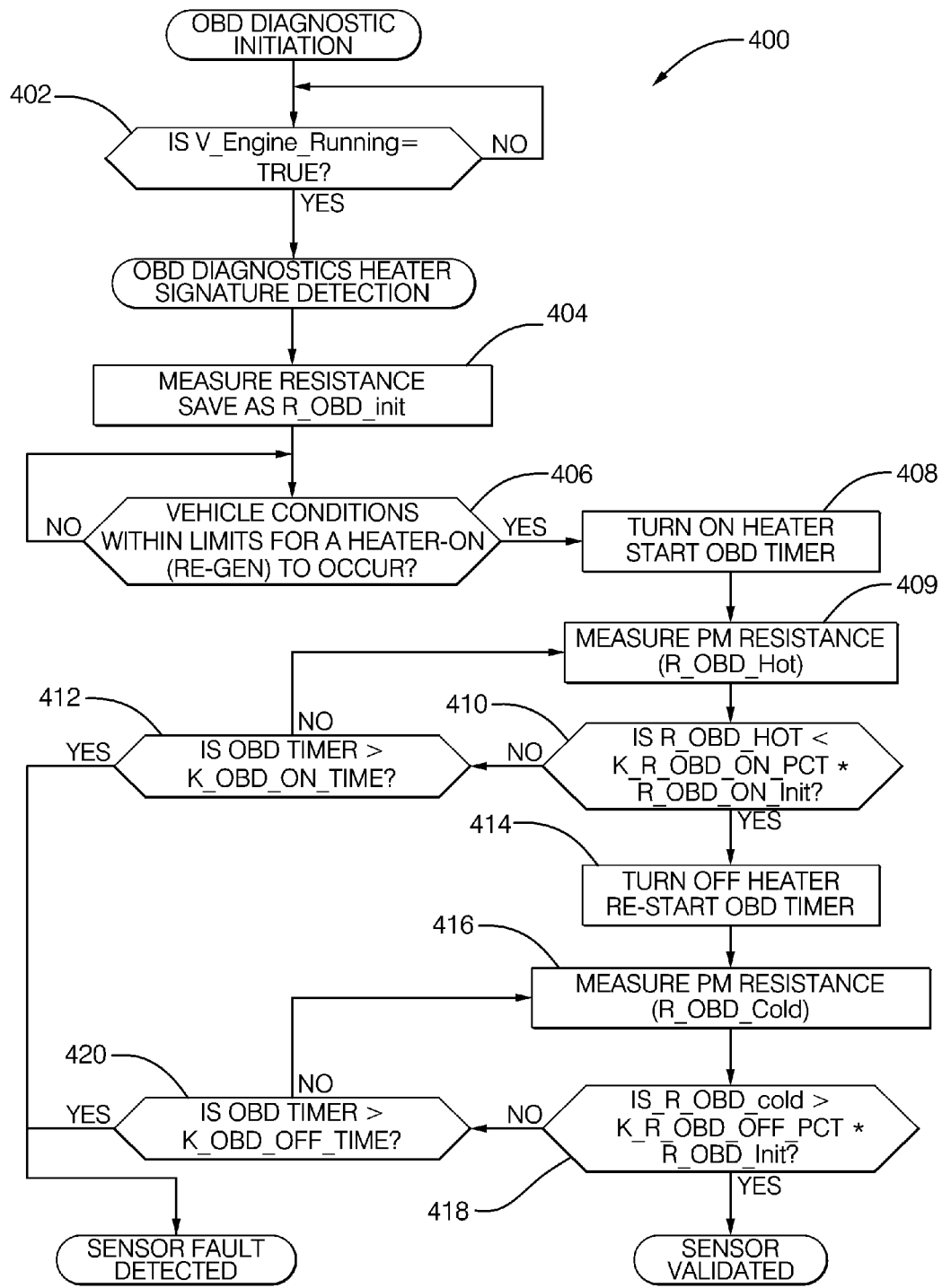
FIG. 5 constitutes a schematic illustration of a flow chart illustrating portions of a control algorithm contemplated for use in exemplary embodiments of the present invention.

Turning now to FIG. 5, a flow chart 400 illustrating portions of a control algorithm in accordance with an exemplary embodiment of the invention is illustrated for performing diagnostics on a particulate matter sensor based on response to heating of the sensor substrate. In this exemplary embodiment, control algorithm 400 is implemented as the result of an ECM-initiated diagnostic, in which case the algorithm at step 402 determines whether a vehicle engine controlled by the ECM is running, and the algorithm proceeds with the diagnostic only if the engine is running. The next step of the diagnostic routine is to measure the resistance between the sensor electrodes in box 404 and store the value in the ECM as $R_{OBD\_init}$.

The algorithm logic path then moves to decision node 406 where the algorithm assesses whether conditions are within limits for a heater-based regeneration of the particulate matter to occur. The purpose of this assessment is to ensure that the conditions are satisfactory for the rigorous heating used to induce a measurable electrical conductivity change in the substrate. Such a heating profile may be similar or identical to the heating profile used to burn off accumulated particulate matter during a sensor regeneration. The criteria used to assess whether the conditions are satisfactory may include (but are not limited to): an upstream diesel particulate filter (DPF) not being in regeneration mode itself (as such a regeneration in combination with activation of the heater in the heater signature detection particulate matter sensor diagnostic may cause overheating of the sensor, and also regeneration of the DPF could cause discharge of contaminants from the DPF that could interfere with the particulate matter sensor diagnostic) and/or the air flow exhaust flow volumes not being too high for the heater to sufficiently regenerate (e.g., 75 msec) or too low so as to risk damage to the heater circuit (e.g., 5 m/sec). If the criteria in decision node 406 are not met, the algorithm holds until they are met. Once the criteria in decision node 406 have been met, the algorithm moves on to box 408 to continue the diagnostic.

In box 408, the algorithm turns on the sensor heater and starts a timer using an internal clock of the ECM. In box 408, the heater is initially powered according to a profile where the heat generated is sufficient to evaporate any liquid water such as water vapor condensate that may happen to be present between the electrodes, but not so great as to cause cracking or other damage to the sensor substrate as could happen if high heat were applied before condensate had evaporated. Once gradual heating has been applied long enough to drive off any condensate, greater amounts of heat, sufficient to induce an electrical conductivity change in the substrate, are applied. In one exemplary embodiment where the substrate is an alumina substrate containing approximately 4% $SiO_2$ glass additive(s), the heat is sufficient to induce a temperature between about 500° C. and 800° C., as measurable reductions in the resistance of such materials are observed as temperatures approach and exceed 500° C., and 800° C. is close to the maximum temperature achievable by an exemplary heater.

After box 408, the algorithm proceeds to box 409, which begins a decision loop where the resistance between the electrodes is observed to see if it changes in a manner consistent with the heating of the sensor element. In box 409, resistance between the sensor electrodes is measured and the resulting value is saved as $R_{OBD\_hot}$, and the algorithm moves on to decision node 410.

In decision node 410, the algorithm evaluates the difference between the measured resistance value $R_{OBD\_hot}$ and a predetermined percentage $K_{R\_OBD\_on\_pct}$ (e.g., 80%) of $R_{OBD\_init}$. If $R_{OBD\_hot}$ is not less than the predetermined percentage $K_{R\_OBD\_on\_pct}$ of $R_{OBD\_init}$, then the algorithm proceeds to decision node 412 and compares the elapsed time on the timer that was started in box 408 against a predetermined value $K_{OBD\_on\_time}$, which is set at a level beyond which the heat being applied according to the profile specified for box 408 should have induced the expected change in electrical conductivity. If the elapsed time is greater than the predetermined value $K_{OBD\_on\_time}$, then the algorithm times out and diagnoses a sensor fault. If the elapsed time is not greater than the predetermined value $K_{OBD\_on\_time}$, then the algorithm returns to box 409 for a new measurement of resistance and a continuation of the decision loop.

If the measured resistance value $R_{OBD\_hot}$ is less than the percentage $K_{R\_OBD\_on\_pct}$ of $R_{OBD\_init}$ in decision node 410, then the algorithm proceeds to box 414 where the sensor heater is turned off so that the sensor can cool down. The algorithm then proceeds to box 416 where resistance between the electrodes is measured and the value stored as $R_{OBD\_cold}$.

Box 416 also begins a decision loop where the resistance between the electrodes is observed to see if it changes in a manner consistent with the cooling of the sensor that is expected to occur after the sensor heater element is turned off in box 414. From box 416, the algorithm proceeds to decision node 418, where the algorithm evaluates the difference between the measured resistance value $R_{OBD\_cold}$ and a predetermined percentage (e.g., 95%) of $R_{OBD\_init}$, and if that difference is not greater than the predetermined percentage $K_{R\_OBD\_off\_pct}$ of $R_{OBD\_init}$, then the algorithm proceeds to decision node 420 and compares the elapsed time on the timer, which was re-started in box 414, against a predetermined value $K_{OBD\_off\_time}$, which is set at a level beyond which the sensor should have cooled sufficiently for measured resistance to approach $R_{OBD\_init}$ within the desired limits. If the elapsed time is greater than the predetermined value $K_{OBD\_off\_time}$, then the algorithm times out and diagnoses a sensor fault. If the elapsed time is not greater than the predetermined value $K_{OBD\_on\_time}$, then the algorithm returns to box 416 for a new measurement of resistance and a continuation of the decision loop.

If the measured resistance value $R_{OBD\_cold}$ is greater the percentage $K_{R\_OBD\_off\_pct}$ Of $R_{OBD\_init}$ in decision node 418, then the algorithm diagnoses a validation that the sensor is in proper working order and reports the same to the ECM system diagnostic function.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A method of diagnosing an operating condition of an electrically conductive particulate matter sensor, said sensor comprising a substrate having an electrical resistance that varies with temperature and two electrodes on said substrate adapted to collect particulate matter between the electrodes, thereby establishing an electrically conductive path through collected particulate matter between the electrodes that can be detected by measuring electrical resistance between the electrodes, $R_{elect}$, said method comprising the steps of:
    (a) providing heat to the sensor in an amount sufficient to modify the electrical resistance of the substrate, and detecting whether $R_{elect}$ changes in a manner consistent with heating of the substrate;
    (b) if $R_{elect}$ increases in a manner consistent with heating of the substrate in step (a), then removing the heat provided in step (a) to cool the substrate;
    (c) if $R_{elect}$ does not change in a manner consistent with heating of the substrate in step (a) or $R_{elect}$ does not change in a manner consistent with cooling of the substrate in step (b), then diagnosing a failure condition for the sensor; and
    (d) if $R_{elect}$ changes in a manner consistent with cooling of the substrate in step (b), then diagnosing a validation that the sensor is in proper working condition.

2. A method according to claim 1 wherein said sensor includes a heater element adapted to heat an area between said electrodes, and step (b) comprises the steps of:
    (1) deactivating the heater for a second period of time while periodically measuring $R_{elect}$, and storing the value as $R_{OBD\_cold}$;
    (2) comparing $R_{OBD\_cold}$ to a predetermined percentage $K_{R\_OBD\_off\_pct}$ of $R_{OBD\_init}$;
    (3) if $R_{OBD\_cold}$ is not greater than the predetermined percentage $K_{R\_OBD\_off\_pct}$ of $R_{OBD\_init}$ during said second period of time, then determining that $R_{elect}$ did not change in a manner consistent with heating the substrate; and
    (4) if $R_{OBD\_cold}$ is greater than the predetermined percentage $K_{R\_OBD\_off\_pct}$ of $R_{OBD\_init}$ during said second period of time, then determining that $R_{elect}$ did change in a manner consistent with heating the substrate.

3. A method according to claim 1 wherein said sensor includes a heater element adapted to heat an area between said electrodes, and step (a) comprises the steps of:
    (1) measuring $R_{elect}$ and storing the value as $R_{OBD\_init}$;
    (2) activating the heater element for a first period of time; while periodically measuring $R_{elect}$, and storing the value as $R_{OBD\_hot}$;
    (3) comparing $R_{OBD\_hot}$ a predetermined percentage $K_{R\_OBD\_on\_pct}$ of $R_{OBD\_init}$;
    (4) if $R_{OBD\_hot}$ is not less than the predetermined percentage $K_{R\_OBD\_on\_pct}$ of $R_{OBD\_init}$, then determining that $R_{elect}$ did not change in a manner consistent with heating the substrate; and
    (5) if $R_{OBD\_hot}$ is less than the predetermined percentage $K_{R\_OBD\_on\_pct}$ of $R_{OBD\_init}$ as determined in step (3) during said first period of time, then determining that $R_{elect}$ changed in a manner consistent with heating the substrate.

4. A method according to claim 3 wherein step (b) comprises the steps of:
    (1) deactivating the heater for a second period of time while periodically measuring $R_{elect}$, and storing the value as $R_{OBD\_cold}$;
    (2) comparing $R_{OBD\_cold}$ to a predetermined percentage $K_{R\_OBD\_off\_pct}$ of $R_{OBD\_init}$;
    (3) if $R_{OBD\_cold}$ is not greater than the predetermined percentage $K_{R\_OBD\_off\_pct}$ of $R_{OBD\_init}$ during said second period of time, then determining that $R_{elect}$ did not change in a manner consistent with heating the substrate; and
    (4) if $R_{OBD\_cold}$ is greater than the predetermined percentage $K_{R\_OBD\_off\_pct}$ of $R_{OBD\_init}$ during said second period of time, then determining that $R_{elect}$ did change in a manner consistent with heating the substrate.

5. A diagnostic system for an electrically conductive particulate matter sensor comprising a substrate and two electrodes on said substrate adapted to collect particulate matter between the electrodes, thereby establishing an electrically conductive path through collected particulate matter between the electrodes that can be detected by measuring electrical resistance between the electrodes, $R_{elect}$, said system comprising a microprocessor in communication with the sensor and a storage medium including instructions for causing the microprocessor to implement a method comprising:
    (a) providing heat to the sensor in an amount sufficient to modify the electrical resistance of the substrate, and detecting whether $R_{elect}$ changes in a manner consistent with heating of the substrate;
    (b) if $R_{elect}$ increases in a manner consistent with heating of the substrate in step (a), then removing the heat provided in step (a) to cool the substrate;
    (c) if $R_{elect}$ does not change in a manner consistent with heating of the substrate in step (a) or $R_{elect}$ does not change in a manner consistent with cooling of the substrate in step (b), then diagnosing a failure condition for the sensor; and
    (d) if $R_{elect}$ changes in a manner consistent with cooling of the substrate in step (b), then diagnosing a validation that the sensor is in proper working condition.

6. A diagnostic system according to claim 5 wherein said sensor includes a heater element adapted to heat an area between said electrodes, and step (b) comprises the steps of:
    (1) deactivating the heater for a second period of time while periodically measuring $R_{elect}$, and storing the value as $R_{OBD\_cold}$;
    (2) comparing $R_{OBD\_cold}$ to a predetermined percentage $K_{R\_OBD\_off\_pct}$ of $R_{OBD\_init}$;
    (3) if $R_{OBD\_cold}$ is not greater than the predetermined percentage $K_{R\_OBD\_off\_pct}$ of $R_{OBD\_init}$ during said second period of time, then determining that $R_{elect}$ did not change in a manner consistent with heating the substrate; and
    (4) if $R_{OBD\_cold}$ is greater than the predetermined percentage $K_{R\_OBD\_off\_pct}$ of $R_{OBD\_init}$ during said second period of time, then determining that $R_{elect}$ did change in a manner consistent with heating the substrate.

7. A diagnostic system according to claim 5 wherein said sensor includes a heater element adapted to heat an area between said electrodes, and step (a) comprises the steps of:
(1) measuring $R_{elect}$ and storing the value as $R_{OBD\_init}$;
(2) activating the heater element for a first period of time; while periodically measuring $R_{elect}$, and storing the value as $R_{OBD\_hot}$;
(3) comparing $R_{OBD\_hot}$ a predetermined percentage $K_{R\_OBD\_on\_pct}$ of $R_{OBD\_init}$;
(4) if $R_{OBD\_hot}$ is not less than the predetermined percentage $K_{R\_OBD\_on\_pct}$ of $R_{OBD\_init}$, then determining that $R_{elect}$ did not change in a manner consistent with heating the substrate; and
(5) if $R_{OBD\_hot}$ is less than the predetermined percentage $K_{R\_OBD\_on\_pct}$ of $R_{OBD\_init}$ as determined in step (3) during said first period of time, then determining that $R_{elect}$ changed in a manner consistent with heating the substrate.

8. A diagnostic system according to claim 7 wherein step (b) comprises the steps of:
(1) deactivating the heater for a second period of time while periodically measuring $R_{elect}$, and storing the value as $R_{OBD\_cold}$;
(2) comparing $R_{OBD\_cold}$ to a predetermined percentage $K_{R\_OBD\_off\_pct}$ of $R_{OBD\_init}$;
(3) if $R_{OBD\_cold}$ is not greater than the predetermined percentage $K_{R\_OBD\_off\_pct}$ of $R_{OBD\_init}$ during said second period of time, then determining that $R_{elect}$ did not change in a manner consistent with heating the substrate; and
(4) if $R_{OBD\_cold}$ is greater than the predetermined percentage $K_{R\_OBD\_off\_pct}$ of $R_{OBD\_init}$ during said second period of time, then determining that $R_{elect}$ did change in a manner consistent with heating the substrate.

* * * * *